(12) United States Patent
Dittrich et al.

(10) Patent No.: US 6,945,983 B2
(45) Date of Patent: Sep. 20, 2005

(54) TROCAR SLEEVE WITH A VARIABLE SEALING OPENING

(75) Inventors: Horst Dittrich, Immendingen (DE); Michael Sauer, Tuttlingen (DE); Martin Oberlaender, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 415 days.

(21) Appl. No.: 10/002,248

(22) Filed: Oct. 26, 2001

(65) Prior Publication Data

US 2004/0010230 A1 Jan. 15, 2004

Related U.S. Application Data

(63) Continuation of application No. PCT/EP01/01351, filed on Feb. 8, 2001.

(30) Foreign Application Priority Data

Feb. 26, 2000 (DE) .......................................... 100 09 132

(51) Int. Cl.[7] .............................................. A61B 17/34
(52) U.S. Cl. ...................................... 606/185; 604/264
(58) Field of Search ................................ 606/185, 167; 604/264, 158, 161.01, 164, 246, 249, 256; 251/149.1

(56) References Cited

U.S. PATENT DOCUMENTS

| | | | |
|---|---|---|---|
| 5,209,737 A | 5/1993 | Ritchart et al. | 604/167 |
| 5,458,640 A * | 10/1995 | Gerrone | 604/264 |
| 5,657,963 A * | 8/1997 | Hinchliffe et al. | 251/149.1 |
| 5,779,697 A | 7/1998 | Glowa et al. | 606/185 |

FOREIGN PATENT DOCUMENTS

| | | |
|---|---|---|
| DE | 43 12 147 A1 | 4/1993 |
| EP | 0 834 279 | 9/1994 |

* cited by examiner

Primary Examiner—Vy Q Bui
(74) Attorney, Agent, or Firm—St. Onge Steward Johnston & Reens LLC

(57) ABSTRACT

A trocar sleeve comprises at its proximal side a housing, from the distal side of which a shaft projects. Further, a sealing of elastic material is provided in order to seal an instrument inserted into the trocar sleeve gas-tight into the proximal direction. The sealing comprises a central opening, the diameter of which is variable. A spreading device is provided which is insertable into the sealing, extending same in doing so, whereby the diameter of the central opening is enlargeable.

It is suggested to configure the spreading device as an axially movable sleeve, the ring-shaped front area of which is insertable into the sealing, spreading same in doing so.

16 Claims, 3 Drawing Sheets

TROCAR SLEEVE WITH A VARIABLE SEALING OPENING

CROSSREFERENCE OF PENDING APPLICATION

This application is a continuation of pending international application PCT/EP01/01351 filed on Feb. 8, 2001 and designating US.

BACKGROUND OF THE INVENTION

The invention relates to a trocar sleeve, comprising at its proximal side a housing, from the distal side of which a shaft projects, and with a sealing of elastic material in order to seal an instrument inserted into the trocar sleeve gas-tight into the proximal direction, wherein the sealing comprises a central opening, the diameter of which is variable, wherein the sealing comprises a position of rest in which the central opening comprises a smallest diameter, and comprising a spreading device which can be inserted into the sealing, extending same in doing so, whereby the diameter of the central opening can be enlarged.

Such a trocar sleeve is known from U.S. Pat. No. 5,209,737. The sealing consists herein of four flap-like sealing elements which surround a central opening. Spreading the sealing, wherein the diameter of the central opening is enlarged, is done by the instrument itself that is inserted into the trocar sleeve.

It is disadvantageous herein that the spreading force has to be applied by the inserted instrument or by the handling person, respectively, and, further, there is the danger that, when the instrument is removed, the flap-like sealing elements cock with the instrument, thus impeding the removal.

U.S. Pat. No. 5,458,640 discloses a cannula valve and seal system. The valve seal has a V-shaped cross section and includes two opposing lips which face each other across a slit. A tubular member is introduced into the valve seal for spreading the two opposing lips by moving the two lips laterally.

Trocars serve for effecting an incision into the body through which instruments can be introduced from the outer side into the body for the minimal-invasive surgery. A trocar consists of a trocar sleeve and, for setting the trocar, of a trocar arbor having a sharpened top in most cases. After setting the trocar, the trocar arbor is removed, and the trocar sleeve remains in the incision in the body. During minimal-invasive surgeries, different instruments are introduced through the trocar sleeve, e.g. endoscopes, medical forceps or other instruments provided with a long shaft. In this operation technique, it is further common to supply a gas into the body cavity in order to insufflate same. To this end, in most cases, a laterally projecting gas supply having a cock is provided in the region of the housing of the trocar sleeve.

As mentioned before, numerous different instruments are introduced or removed, respectively, through the trocar sleeve in the course of a minimal-invasive surgery.

In order to prevent gas from escaping from the body, either a flap valve is provided which automatically closes the trocar sleeve gas-tight versus the proximal direction, if no instrument is introduced into the sleeve, or a sealing is provided in the form of a slotted sealing, mostly at the transition between housing and shaft which can be pushed through and expanded by the instrument. It is true that this sealing can provide for a gas-tight seal, if no instrument is introduced, but due to the slotted geometry, a gas-tight seal is not possible with respect to the shaft of the introduced instrument having mostly a circle-round cross section.

For this reason, a sealing is provided in the trocar sleeve which comprises a central opening, the diameter of which corresponds approximately to the outer diameter of the shaft of the introduced instrument.

In other words, the sealing of elastic material comprises such an opening that the instrument can just be pushed through it and a gas-tight seal is nevertheless guaranteed.

As mentioned above, however, it is necessary that instruments having different shaft diameters can be introduced through the trocar sleeve.

If one takes a trocar sleeve having a clear inner diameter of 11 mm as an example, instruments having a shaft outer diameter of between 5 and 10 mm are usually introduced through the trocar sleeve.

If the sealing has an opening with a diameter of just 5 mm, an instrument having a shaft diameter of 6 mm could just be moved through the sealing by overcoming a resistance.

If, however, an instrument having a shaft diameter of 10 mm is to be introduced through this sealing, this is, if at all, only possible by applying a lot of force. Even if one should have succeeded in introducing an instrument having a shaft diameter of 10 mm through the opening having a size of 5 mm, it would be very disturbing and difficult for the operating person to move the instrument axially to-and-fro during the surgery. This will, at best, be performed in jerks, which is not desired.

It is an object of the present invention to improve a trocar sleeve having a sealing with a variable opening diameter in such a way that the enlarging process can be selectively performed and a safe sealing is guaranteed for different instrument diameters.

SUMMARY OF THE INVENTION

This object is achieved according to the invention by the spreading device comprising an axially movable sleeve, the ring-shaped front area of which is insertable into a disk-shaped portion of the sealing.

In the position of rest, the sealing is unstressed, and the opening may e.g. comprise a diameter which corresponds to the outer diameter of a smallest shaft diameter that is to be introduced through the trocar sleeve.

If an instrument having a greater shaft diameter is to be introduced, the spreading device is actuated which enters the sealing and expands same in doing so, whereby the diameter of the central opening is enlarged. In this procedure, the spreading process is performed by the spreading device and not by the instrument itself, so that the spreading process can be performed prior to introducing the instrument.

For introducing, it is e.g. possible to extend the opening even a little bit wider than necessary, so that the instrument can be introduced into the body through the trocar sleeve more or than less without touch and, thus, simply and with low resistance. Due to the elasticity of the material, a restoring force is created during the extending process which results in the sealing being brought back into its position of rest. If then the spreading device is released again, the opening is contracted, and the sealing material adjoins around the shaft-shaped outer side of the meanwhile introduced instrument with the required sealing pressure. In that way, the necessary gas-tight forcing pressure is guaranteed.

The extending force acts evenly around the opening onto the sealing by the ring-shaped front area of the movable sleeve which simultaneously causes correspondingly radial spreading forces in order to enlarge the circle-shaped opening, i.e. by maintaining this circle geometry. The sleeve may be inserted into the tubular housing of the trocar sleeve in a space-saving manner and leaves empty the necessary central space to introduce instruments or the trocar arbor or opturators.

For removing the instrument, the spreading device may then be pushed in again, so that the instrument can then simply be removed, i.e. without frictional resistance.

If the axial introduction depth of the instrument is to be modified, the spreading device can be drawn in so far that the instrument can be displaced without a remarkable gas outlet taking place. The handling of the instrument is, thus, additionally facilitated.

The sealing comprises a disk-shaped portion that extends transversally to the trocar sleeve axis in which the opening is provided in the center.

This measure has the advantage that the sealing in its position of rest requires low construction space and can, thus, also be manufactured in a simple and cost effective manner. This geometry allows an even expanding of the opening in the axially extending process by maintaining the circle geometry.

In another embodiment it is provided that the ring-shaped front area of the sleeve is arranged coaxially to the circle-shaped opening in a disk-shaped portion of sealing.

This geometrical embodiment provides, on the one hand, for a gentle force transmission for extending the sealing and ensures an enlargement of the circle-round opening by keeping the circle geometry.

In another embodiment of the invention, the sealing comprises a pot-shaped body, in the bottom of which the opening is provided, and the sleeve of the spreading device is insertable into the body and extends same axially.

This measure has the advantage that the geometry of the pot has already basically designed the deformation process of the sealing, i.e. the pot, similar to a deep-drawing process is extended to a deep basin, the bottom of which then provides material to form the longer pot wall, wherein the central opening of the pot expands or enlarges. The geometry of the pot herein favors the maintaining of the circle geometry when the opening is enlarged.

In another embodiment of the invention, sealing and sleeve are arranged in the housing.

This measure has the advantage that these components of the spreading device are protectively located in the inner part of the trocar sleeve and require no space-seizing measures, so that if the trocar sleeve is slenderly constructed, a maximal clear inner space for introducing and leading instruments through is available.

In another embodiment of the invention, the spreading device is fixable in different insert positions.

This measure has the considerable advantage that the opening of the sealing is expanded to certain diameter sizes and is then kept in this extended or expanded state by the determined spreading device.

The more the opening is enlarged, the more advantageous is the measure. To cite the example already repeatedly mentioned, namely a sealing that has a opening diameter of 5 mm in the position of rest, i.e. in the unstressed position, the restoring force will be still relatively low after spreading onto a diameter of approximately 6 mm and allows the operating person to move an instrument having such a diameter to-and-fro in the spreaded sealing in order to correct the axial position. If, however, the opening is spreaded to a diameter of 10 mm, the restoring force will be much stronger, and an axial displacement will only be possible by overcoming a considerable frictional resistance.

If the spreading device is fixed in a draw-in position that has just caused an expanding of the opening onto 10 mm, the instrument can then be axially moved to-and-fro in the sealing. It has merely to be provided that the pressure force is sufficient to create a gas-tight seal. This can be achieved e.g. by spreading the sealing merely to 9.95 mm.

In another embodiment of the invention, a guide is provided through which the displacing movement of the spreading device is guidable, and locking means are provided in order to interlock the spreading device in certain displacing positions.

This measure has the advantage that displacing movements clearly predetermined by the guide result which can be easily carried out by the operating person without particular attention and which can be easily carried out from one interlocking position to the other, so that then exactly defined sealing opening sizes can be reached and it can be varied between them.

In another embodiment of the invention, the guide comprises a slot-link guide, alongside of which a movable member is guidable.

In another embodiment of the invention, the slot-link guide is configured as a heart curve, so that the spreading device is movable between a zero position, without spreading the sealing, a maximal spreading position and intermediate spreading positions therebetween.

This measure has the considerable handling advantage that from the zero position by positioning the device alongside of the heart curve, it can first of all be brought into the maximal spreading position, for introducing a great diameter instrument through the opening nearly without contact. The sealing will then be moved into an intermediate spreading position, a spreading position that is ideal just for the instrument introduced. In the next movement cycle, the spreading is performed from this intermediate position onto the maximal spreading position, namely in order to remove the instrument again. In the next cycle, the spreading device moves again into the zero position from the maximal spreading position, i.e. the sealing is unstressed again.

In order to illustrate that by means of a numerical example, it is returned to the numerical example that has been mentioned before already several times. If the sealing has at its starting point, i.e. in the zero position, an opening diameter of 5 mm and if an instrument is to be introduced with a shaft diameter of 10 mm, the opening can, first of all, be expanded to a maximal diameter of 11 mm. By means of this opening that has been expanded a bit too much, the instrument can be introduced through the sealing without much friction and can be axially brought into the suitable insert position. In the second moving cycle, alongside the heart curve, the sealing is now tapered from a diameter of 11 mm to 10 mm, i.e. it lies in an exactly fitting manner at the shaft of the instrument having an outer diameter of 10 mm. The force pressure is sufficient to guarantee a gas-tight seal, nevertheless, the instrument can axially somewhat be moved to-and-fro. If the instrument is to be removed again, by conducting further in the heart curve, the opening is, first of all, expanded from 10 mm to 11 mm, then, the instrument can simply be removed again. In the fourth moving cycle, the device is then conducted back from the maximal spreading position (11 mm) into the initial position, so that then the sealing takes up its unstressed position again, i.e. the zero position with an opening diameter of 5 mm.

In another embodiment of the invention, the spreading device comprises an actuation member which can be actuated from the outer side of the trocar sleeve.

This measure has the advantage that the actuation member can be acted from the outer side by the operating person, however, all other components can be arranged in the inner part of the trocar sleeve in a protected manner.

In another embodiment of the invention, the actuation member is configured as a lever which is pivotable about an axis that extends transversally to the trocar sleeve axis.

This constructive arrangement makes it possible for the operating person to apply a finger or a thumb onto the lever, to press same into axial direction and, thus, move the spreading device. This movement direction is not only ergonomic for the operating person, but also prevents the undesired turning movements of a trocar sleeve in the incision.

In another embodiment of the invention, a pin projects from the lever which runs in the guide.

In another embodiment of the invention, the pin is spring biased.

This measure has the advantage that the pin is guided in an exactly safe manner in the guide or is pressed into same, respectively, so that, for instance, the guide can be supported by suitable bevels, the spring biased pin following same exactly.

It is to be understood that the features mentioned above and those yet to be explained below can be used not only in the respective combinations indicated, but also in other combinations or in isolation, without leaving the scope of the present invention.

BRIEF DESCRIPTION OF THE DRAWINGS

An embodiment of the invention is described and explained in more detail. In the drawings.

DETAILED DESCRIPTION OF A PREFERRED EMBODIMENT

Figure 1:
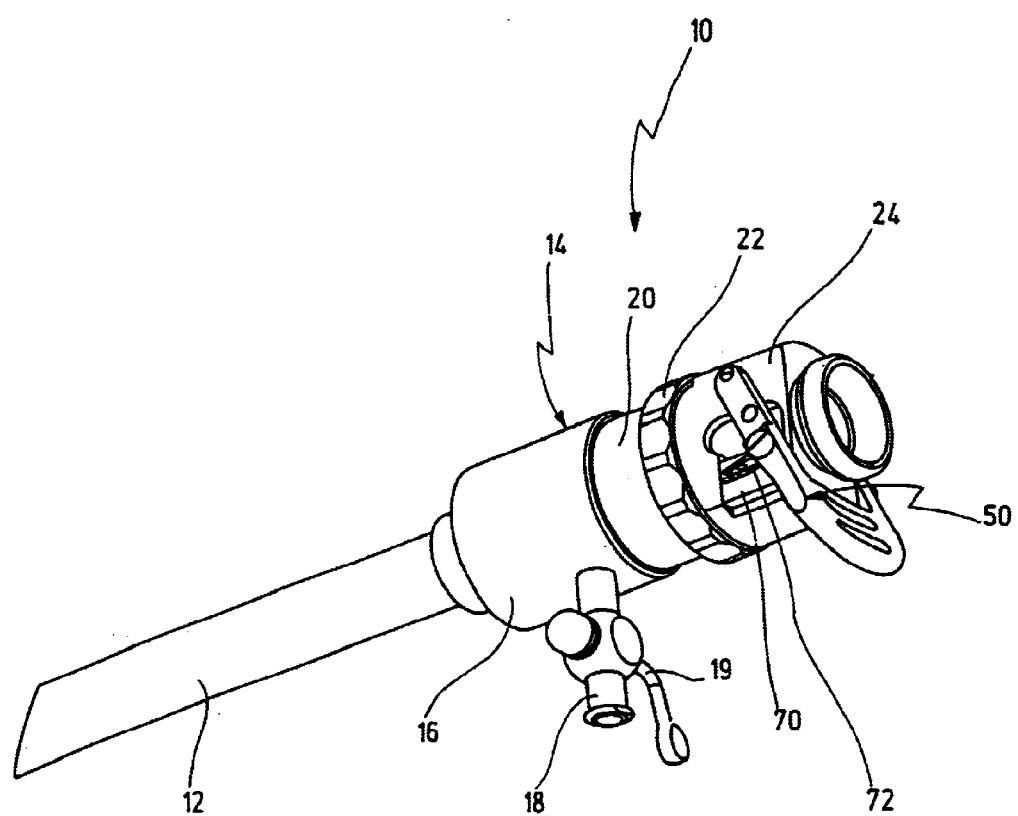
FIG. 1 shows a perspective view of a trocar sleeve having a spreading device according to the invention.

A trocar sleeve shown in FIG. 1 is altogether provided with the reference numeral 10.

Trocar sleeve 10 comprises a shaft 12, on the proximal sided end of which a housing 14 is arranged.

Housing 14 comprises an approximately hollow cylindrical outer portion 16 which adjoins directly at the proximal end of hollow shaft 12. From outer portion 16, a gas supply 18 radially protrudes which can be opened and closed via a cock 19. Via gas supply 18, a gas can be led into the inner space of housing 14 and through shaft 12.

Figure 2:
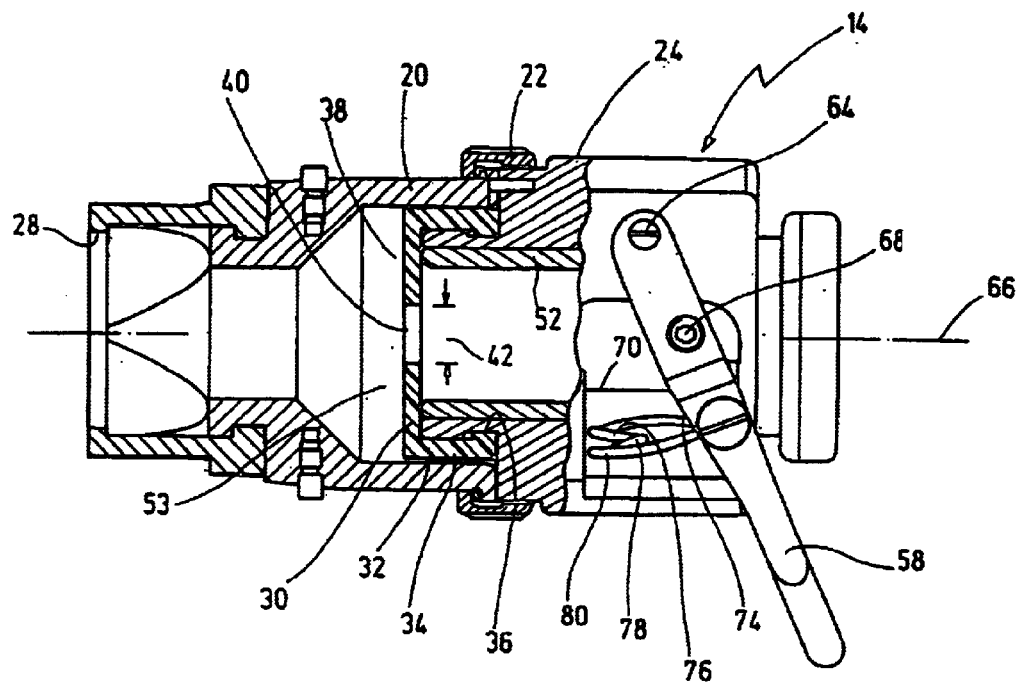
FIG. 2 shows a lateral view, partly in the longitudinal section of a proximal end region of the trocar sleeve of FIG. 1 in a position with not spread sealing.
Figure 3:
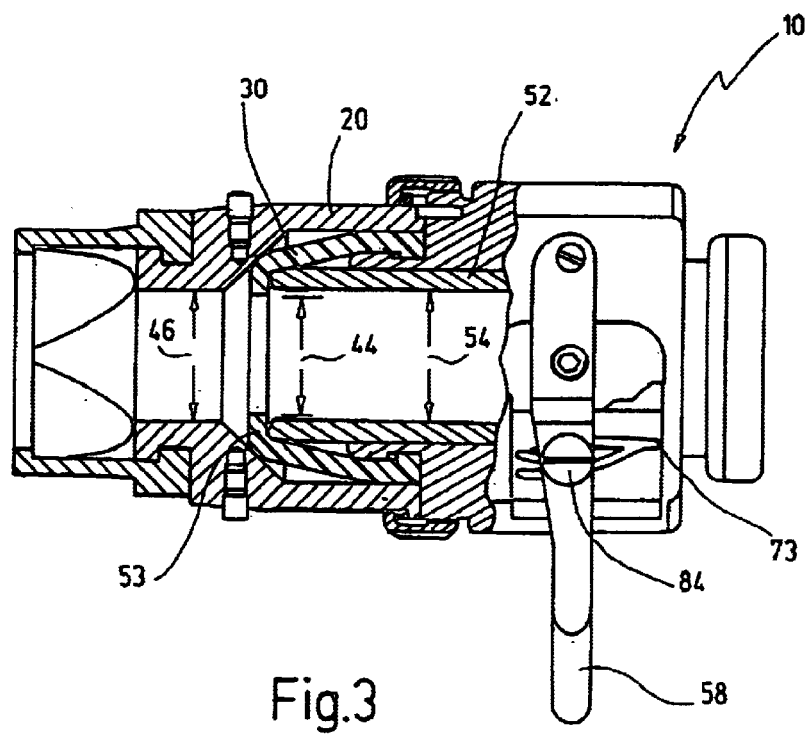
FIG. 3 shows a view corresponding to FIG. 2 with a spread sealing.

As can be seen in particular from the sectioned descriptions of FIGS. 2 and 3, housing 14 comprises an inner tube-shaped portion 20 which is inserted into outer portion 16 from proximal. An end section 24 is fixed at the proximal end of inner portion 20 via a coupling nut 22.

It can be seen from FIG. 2 that at the distal sided end of inner portion 20 a slotted sealing 28 is fixed i.e. which extends until into outer portion 16.

This slotted sealing 28 serves for sealing the shaft at the proximal side.

This sealing seals gas-tightly, if, like in the sectioned description, no instrument or no object, like a trocar arbor or an obturator, is introduced into trocar sleeve 10.

At the proximal side of slotted sealing 28, a sealing 30 is provided.

Sealing 30 has an approximately pot-shaped body 32.

Body 32 comprises a ring 34 or a tube section, the axis of which extends alongside trocar sleeve axis 66. At the proximal end, a flange 36 protruding to the inner side protrudes. At the opposite end, body 32 is provided with an approximately flat bottom 38 which comprises an opening 40 in its center. Said bottom 38 is a disk-shaped portion of sealing 30. Bottom 38 extends vertically to trocar sleeve axis 66 in a cross sectional plane. Opening 40 comprises a diameter 42, in the embodiment shown 5 mm.

Sealing 30 is clamped between inner portion 20 and end section 24 and is firmly held there in the region of its ring-shaped section 34 and of flange 36.

A spreading device 50 is provided for enlarging diameter 42, i.e. to spread opening 40.

Spreading device 50 comprises a sleeve 52, the outer diameter of which corresponds approximately to the clear inner diameter of end section 24. The clear inner diameter of sleeve 52 is so large that it corresponds at least to the maximal clear inner diameter of the passage through housing 14 of trocar sleeve 10, as indicated by diameter 46 in FIG. 3.

It can be seen from FIG. 2 that a distal sided ring-shaped front area 53 of sleeve 52 sits on bottom 38 of sealing 30, namely in such a way that front area 53 coaxially circles circle-round opening 40. At the outer side of end section 24, a lever 58 is arranged which comprises two prongs 60 and 62 which adjoin approximately tangentially diametrically at the outer side, as can particularly be seen from the top view of FIG. 5. On a side opposite to the actuation area of lever 58, prongs 60 and 62 are connected with housing 14 via screws, the centered longitudinal axis of the housing representing a pivot axis 64 of lever 58.

Figure 4:
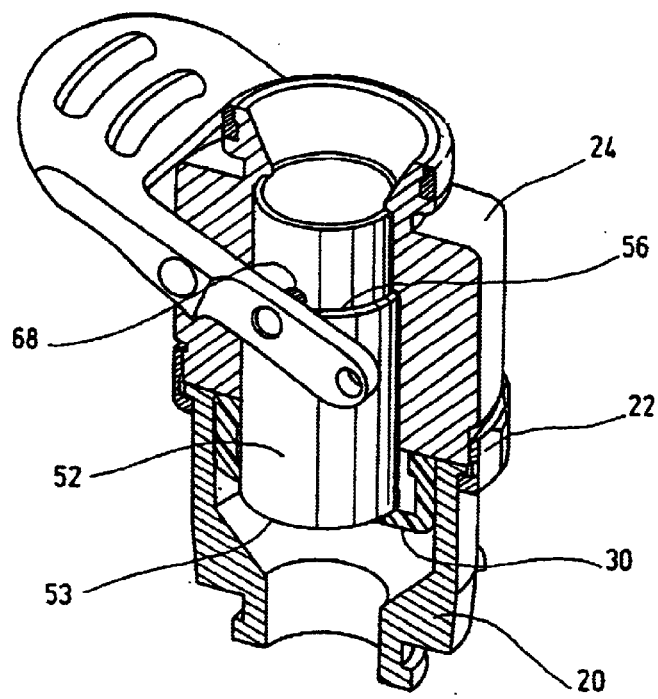
FIG. 4 shows a perspective, partly sectioned lateral view of the proximal end region of the trocar sleeve of FIG. 1.

Distanced from pivot axis 64, from prongs 60 and 62, each a pivot 68 protrudes radially to the inward which rests on annular shoulder 56 of sleeve 52, as can be seen from the description in FIG. 4.

If lever 58 is pressed into the distal direction, as corresponds to the passage from FIG. 2 to FIG. 3, pivot 68 presses sleeve 52 into the distal direction, i.e. same is moved alongside trocar sleeve 10. As front area 53 rests on bottom 38 of sealing 30, sealing 30 is stretched in doing so, and in doing so, opening 40 is expanded, as can be seen by the passage from FIG. 2 to FIG. 3.

Sleeve 52 is introduced into pot-shaped body 32, extending same axially, wherein opening 40 in the bottom is radially expanded. Material of bottom 38 flows radially to the outward to form the lengthened or radially extended pot shape, respectively, in this procedure, opening 40 is spread. In order to facilitate this material flow, front area 53 of sleeve 52 is rounded.

In FIG. 3, a position is shown in which sealing 30 is in an intermediate spreading position, though not far from a maximal spreading position. In the view of FIG. 3, the diameter of opening 40 has enlarged to intermediate diameter 44, in the embodiment shown 10 mm. By further pressing lever 58 into the distal direction, sleeve 52 can be shifted somewhat further, so that then sealing 30 is still extended a bit more and spreads opening 40 still somewhat further, namely until to maximal diameter 46, in the embodiment shown 11 mm.

In the embodiment shown, a slot-link guide is provided through which the movements of lever 58, i.e. correspondingly of sleeve 52 and, hence, the spreading widths of opening 40 are predetermined.

To this end, at the outer side, a segment is provided in the form of a sliding block 70, in which a guide 71 is recessed in the form of a heart curve 72.

As can be seen in particular from FIG. 2, heart curve 72 comprises a first portion 74, at which adjoins a returning short second portion 76. At same, a forwarding third portion 78 adjoins, from the outer end of which a fourth portion 80 leads back to the starting point of first portion 74.

Figure 5:
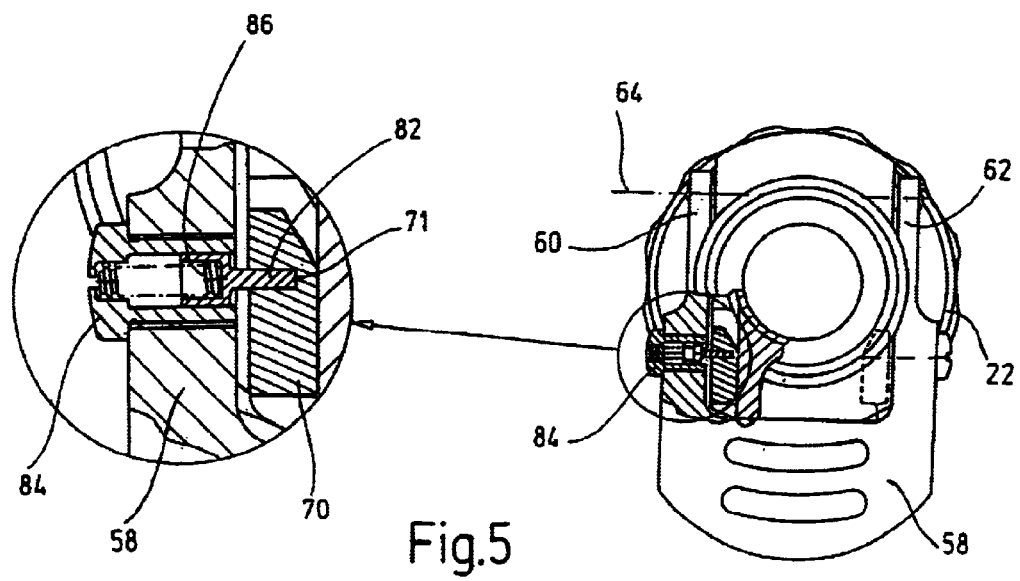
FIG. 5 shows a front area view of the proximal end of the trocar sleeve of FIG. 1 with a partial section in the region of the control of the spreading device, wherein the region circled with a circle is shown again in a highly enlarged size.

As can particularly be seen from the view of FIG. 5, from the inner side of prongs 60 of lever 58, a pin 82 protrudes which is received in the inner cavity of a nut 84 in which a biased spring is located which biases pin 82 such that it is pressed out of the nut.

Pin 82 now runs in heart curve 72 which is cut out in sliding block 70. The embodiment shall be described in more detail by means of the functioning.

In FIG. 2, a position is shown in which lever 58 is in its maximally shifted proximal direction, i.e. pin 82 comes to lying in the region of outermost tip 73 (see FIG. 3) of heart curve 72.

This corresponds to the position of rest of sealing 30, i.e. it is in a zero-spreading position, i.e. not extended.

If lever 58 is pressed into the distal direction, pin 82 moves forcibly in the first portion 74 of heart curve 72, and it can be advanced so far until the distal sided end of first portion 74 is reached. In this state, sleeve 52 is maximally advanced into the distal direction, sealing 30 is maximally extended, and opening 40 is maximally extended until its maximal diameter 46 (e.g. 11 mm).

In this maximally extended or spread state, an instrument having a shaft outer diameter of 10 mm can now, for example, be introduced into the body through trocar sleeve 10. If lever 58 is released, it forcibly moves somewhat back in the second portion 76 of heart curve 72. This is reached by the fact that second portion 76 is somewhat deeper cut in and pin 82 is forcibly pressed into this path via spring 86.

Lever 58 moves back so far until it comes to lying in the basin of the heart-shaped recess cut, i.e. at the proximal end of second portion 76, this position is shown in FIG. 3. Sleeve 52 is in this procedure somewhat returned, wherein this is performed by the restoring force of the elastic material of sealing 30.

Opening 40 now has taken the intermediate spreading position with opening diameter 44 (10 mm) and lies then with a sufficient force pressure at the outer side of the corresponding shaft (not shown here) of the inserted instrument. Lever 58 remains then in the position shown in FIG. 3, i.e. is interlocked in this position.

When lever 58 is pressed again, same is moved from proximal to distal alongside short third portion 78 of heart curve 72. This is also forcibly effected by pressing pin 82 into this path of third portion 78 via spring 86. In that procedure, sealing 30 is spread again to maximal diameter 46, so that now the instrument with the outer diameter 10 mm can simply be removed from trocar sleeve 10. After that, lever 58 is released and moves alongside fourth portion 80 back again to the starting point of heart curve 72, i.e. to its tip 73. This movement is, again, forcibly controlled, as pin 82 is pressed from third portion 78 into this fourth portion 80 by spring 86. The restore is performed again via the elasticity or the restoring force of the material of sealing 30, respectively, so that lever 58 is again in the position shown in FIG. 2.

What is claimed is:

1. A trocar sleeve, comprising
   a housing,
   a shaft projecting from a distal side of said housing,
   a sealing made of an elastic material, said sealing being provided for sealing an instrument inserted into said trocar sleeve in a gas-tight manner versus a proximal direction of said sealing,
   said sealing having a disk-shaped portion extending transversally to a longitudinally axis of said trocar sleeve,
   a central opening being provided in said disk-shaped portion of said sealing, said central opening having a smallest diameter in a first, not yet stretched rest position of said sealing, and a spreading device for stretching said elastic material of said sealing in a manner to enlarge said diameter of said central opening,
   said spreading device comprising a sleeve being movable along said longitudinal axis of said trocar sleeve, a ring-shaped facial end of said movable sleeve resting on said disk-shaped portion of said sealing, and
   a lock mechanism comprising at least three lock positions wherein said spreading device is not movable, said at least three lock positions comprising a zero position without stretching and spreading said sealing, a second position of a maximum stretching of said sealing, and at least one intermediate position between said zero position and said second maximum stretching position for intermediate spreading of said sealing.

2. The trocar sleeve of claim 1, wherein said ring-shaped facial end of said movable sleeve is arranged coaxially to said central opening in said disk-shaped portion of said sealing, said central opening being circle-shaped.

3. The trocar sleeve of claim 1, wherein said sealing has a pot-shaped body, said central opening being provided in a bottom of said pot-shaped body, and said movable sleeve being insertable into said pot-like body for stretching said bottom thereby enlarging said diameter of said central opening.

4. The trocar sleeve of claim 3, wherein said pot-shaped body of said sealing and said movable sleeve are arranged in said housing.

5. The trocar sleeve of claim 1, wherein said spreading device being fixable in different positions which different positions correspond to differently enlarged diameters of said central opening of said sealing.

6. The trocar sleeve of claim 1, wherein a guide is provided for guiding a displacing movement of said spreading device, and wherein said lock mechanism is provided for interlocking said spreading device in different displacing positions.

7. The trocar sleeve of claim 6, wherein said guide comprises a slot-link guide, a slidable member is guided within said slot-link guide.

8. The trocar sleeve of claim 7, wherein said slot-link guide is configured as a heart curve guide.

9. The trocar sleeve of claim 6, wherein said spreading device comprises an actuation member which can be activated from an outer side of said trocar sleeve.

10. The trocar sleeve of claim 9, wherein said actuation member is configured as a lever being pivotable about an axis extending transversally to said longitudinally extending trocar sleeve axis.

11. The trocar sleeve of claim 10, wherein said lever is provided with a pin, said pin acts as said movable member moving along said slot-link guide.

12. The trocar sleeve of claim 11, wherein said pin being forced by a spring.

13. The trocar sleeve of claim 1, wherein the at least one intermediate position comprises substantially any position between said zero position and said second maximum stretching position.

14. The trocar sleeve of claim 1, wherein the at least one intermediate position comprises a plurality of intermediate positions.

15. A trocar sleeve, comprising a housing, a shaft projecting from a distal side of said housing, a sealing made of an elastic material, said sealing being provided for sealing an instrument inserted into said trocar sleeve in a gas-tight manner versus a proximal direction of said sealing, said sealing having a disk-shaped portion extending transversally to a longitudinally axis of said trocar sleeve, a central opening being provided in said disk-shaped portion of said sealing, said central opening having a smallest diameter in a first, not yet stretched rest position of said sealing, and a spreading device for stretching said elastic material of said sealing in a manner to enlarge said diameter of said central opening, said spreading device comprising a sleeve being movable along said longitudinal axis of said trocar sleeve, a ring-shaped facial end of said movable sleeve resting on said disk-shaped portion of said sealing, wherein a guide is provided for guiding displacement of said spreading device between a zero position without stretching and spreading said sealing, a position of a maximum stretching of said sealing, and intermediate spreading positions of said sealing between said zero position and said maximum stretching position, and a lock for interlocking said spreading device in said different positions.

16. A trocar sleeve, comprising a housing, a shaft projecting from a distal side of said housing, a sealing made of an elastic material, said sealing being provided for sealing an instrument inserted into said trocar sleeve in a gas-tight manner versus a proximal direction of said sealing, said sealing having a disk-shaped portion extending transversally to a longitudinally axis of said trocar sleeve, a central opening being provided in said disk-shaped portion of said sealing, said central opening having a smallest diameter in a first, not yet stretched rest position of said sealing, and a spreading device for stretching said elastic material of said sealing in a manner to enlarge said diameter of said central opening, said spreading device comprising a sleeve being movable along said longitudinal axis of said trocar sleeve, a ring-shaped facial end of said movable sleeve resting on said disk-shaped portion of said sealing, a lock mechanism is provided for interlocking said spreading device in different displacing positions, and a guide is provided for guiding a displacing movement of said spreading device said guide comprising a slot-link guide and a slidable member guided within said slot-link guide, wherein said slot-link guide is configured as a heart curve guiding said spreading device between a zero position without stretching and spreading said sealing and a position of a maximum stretching said sealing and with intermediate spreading positions being between said zero position and said maximum stretching position.

* * * * *